United States Patent
Yamanaka (10) Patent No.: US 11,260,544 B2
(45) Date of Patent: Mar. 1, 2022

(54) FORCE TRANSMITTING MECHANISM AND INSTRUMENT

(71) Applicant: OLYMPUS CORPORATION, Tokyo (JP)

(72) Inventor: Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 181 days.

(21) Appl. No.: 16/596,853

(22) Filed: Oct. 9, 2019

(65) Prior Publication Data

US 2020/0039093 A1 Feb. 6, 2020

Related U.S. Application Data

(63) Continuation of application No. PCT/JP2017/015476, filed on Apr. 17, 2017.

(51) Int. Cl.
*A61B 17/29* (2006.01)
*B25J 17/02* (2006.01)
*B25J 15/02* (2006.01)

(52) U.S. Cl.
CPC .......... *B25J 17/0266* (2013.01); *A61B 17/29* (2013.01); *B25J 15/022* (2013.01); *A61B 2017/2901* (2013.01); *A61B 2017/2927* (2013.01); *A61B 2017/2939* (2013.01); *A61B 2017/2947* (2013.01)

(58) Field of Classification Search
CPC .... A61B 2017/2932; A61B 2017/2939; A61B 2017/2941; A61B 2017/2927; A61B 2017/2901; A61B 2017/2947; A61B 34/30; A61B 17/29; B25J 15/022; B25J 17/0266

See application file for complete search history.

(56) References Cited

U.S. PATENT DOCUMENTS 6,193,717 B1 2/2001 Ouchi
6,258,087 B1 7/2001 Edwards et al.
(Continued)

FOREIGN PATENT DOCUMENTS

EP 2113210 A2 11/2009
JP 2004-129871 A 4/2004
(Continued)

OTHER PUBLICATIONS

International Search Report dated Jun. 13, 2017 issued in PCT/JP2017/015476.

*Primary Examiner* — Majid Jamialahmadi (74) *Attorney, Agent, or Firm* — Scully, Scott, Murphy & Presser, P.C.

(57) ABSTRACT

A force transmitting mechanism includes: a force adjusting portion that is disposed between a joint portion of an instrument and a force generating portion and that receives force from the force generating portion; and a driving member that passes through the joint portion, that connects the end effector and the force adjusting portion, and that transmits the force applied from the force adjusting portions to the end effector, wherein, by means of displacement of the driving member associated with flexing or bending of the joint portion, the force adjusting portion increases the force transmission efficiency so that an amount of increase in the force transmission efficiency increases with an increase in a displacement amount of the driving member.

7 Claims, 7 Drawing Sheets

(56) References Cited

U.S. PATENT DOCUMENTS

| | | |
|---|---|---|
| 6,428,538 B1 | 8/2002 | Blewett et al. |
| 6,676,659 B2 | 1/2004 | Hutchins et al. |
| D767,353 S | 9/2016 | Miller et al. |
| 2003/0036768 A1 | 2/2003 | Hutchins et al. |
| 2004/0249411 A1* | 12/2004 | Suzuki ................ A61B 17/29 606/205 |
| 2005/0090847 A1 | 4/2005 | Hutchins et al. |
| 2005/0192607 A1 | 9/2005 | Hutchins et al. |
| 2005/0192610 A1 | 9/2005 | Houser et al. |
| 2005/0234338 A1 | 10/2005 | Masuda |
| 2005/0273084 A1 | 12/2005 | Hinman et al. |
| 2005/0273085 A1 | 12/2005 | Hinman et al. |
| 2006/0079874 A1 | 4/2006 | Faller et al. |
| 2006/0079875 A1 | 4/2006 | Faller et al. |
| 2006/0079876 A1 | 4/2006 | Houser et al. |
| 2006/0079877 A1 | 4/2006 | Houser et al. |
| 2006/0079878 A1 | 4/2006 | Houser |
| 2006/0079879 A1 | 4/2006 | Faller et al. |
| 2007/0282332 A1 | 12/2007 | Witt et al. |
| 2007/0282333 A1 | 12/2007 | Fortson et al. |
| 2007/0282334 A1 | 12/2007 | Young et al. |
| 2007/0282335 A1 | 12/2007 | Young et al. |
| 2008/0097501 A1 | 4/2008 | Blier |
| 2009/0223033 A1 | 9/2009 | Houser |
| 2009/0270853 A1 | 10/2009 | Yachi et al. |
| 2010/0023044 A1 | 1/2010 | Houser et al. |
| 2010/0094087 A1 | 4/2010 | Hutchins et al. |
| 2010/0222713 A1 | 9/2010 | Faller et al. |
| 2010/0234831 A1 | 9/2010 | Hinman et al. |
| 2010/0249759 A1 | 9/2010 | Hinman et al. |
| 2012/0123441 A1 | 5/2012 | Au et al. |
| 2012/0253373 A1 | 10/2012 | Young et al. |
| 2012/0296327 A1 | 11/2012 | Hutchins et al. |
| 2013/0060239 A1 | 3/2013 | Hinman et al. |
| 2013/0218141 A1 | 8/2013 | Hinman et al. |
| 2013/0338691 A1 | 12/2013 | Young et al. |
| 2014/0058426 A1 | 2/2014 | Hutchins et al. |
| 2014/0243863 A1 | 8/2014 | Faller et al. |
| 2015/0119903 A1 | 4/2015 | Hinman et al. |
| 2015/0245849 A1 | 9/2015 | Young et al. |
| 2015/0289942 A1 | 10/2015 | Au et al. |
| 2015/0297865 A1 | 10/2015 | Hinman et al. |
| 2016/0256217 A1 | 9/2016 | Hutchins et al. |
| 2016/0030120 A1 | 10/2016 | Haas et al. |
| 2017/0177521 A1 | 6/2017 | Singleton et al. |
| 2017/0304014 A1 | 10/2017 | Au et al. |
| 2018/0104448 A1 | 4/2018 | Hinman et al. |
| 2018/0221049 A1 | 8/2018 | Faller et al. |

FOREIGN PATENT DOCUMENTS

| | | |
|---|---|---|
| JP | 2008-000611 A | 1/2008 |
| JP | 2008-501478 A | 1/2008 |
| JP | 2009-56131 A | 3/2009 |
| JP | 2009-261911 A | 11/2009 |
| JP | 2012-066102 A | 4/2012 |
| JP | 2012-210445 A | 11/2012 |
| JP | 2013-240612 A | 12/2013 |
| JP | 2014-504897 A | 2/2014 |
| JP | 2016-512961 A | 5/2016 |
| JP | 2017-205536 A | 11/2017 |
| WO | WO 2005/120327 A2 | 12/2005 |
| WO | WO 2006/042210 A2 | 4/2006 |
| WO | WO 2007/143439 A2 | 12/2007 |
| WO | WO 2012/064528 A1 | 5/2012 |
| WO | WO 2014/123245 A1 | 8/2014 |

\* cited by examiner

FORCE TRANSMITTING MECHANISM AND INSTRUMENT

CROSS-REFERENCE TO RELATED APPLICATIONS

This is a continuation of International Application PCT/JP2017/015476, with an international filing date of Apr. 17, 2017, which is hereby incorporated by reference herein in its entirety.

TECHNICAL FIELD

The present invention relates to a force transmitting mechanism and an instrument.

BACKGROUND ART

In the related art, there is a known instrument that includes an end effector provided at a distal end thereof and an operating portion provided at a proximal end thereof, and that causes the end effector to execute motions such as opening/closing by transmitting force that an operator applies to the operating portion to the end effector (for example, see Patent Literatures 1 and 2). As a force transmitting member that transmits the force to the end effector from the operating portion, a cable is used in Patent Literature 1 and a wire is used in Patent Literature 2.

CITATION LIST

Patent Literature

{PTL 1} Japanese Unexamined Patent Application, Publication No. 2013-240612
{PTL 2} Japanese Unexamined Patent Application, Publication No. 2009-261911

SUMMARY OF INVENTION

A first aspect of the present invention is directed to a force transmitting mechanism that is provided in an instrument including an end effector, a joint portion that is configured to be flexed or curved, and a force generating portion that generates force and that transmits the force to the end effector from the force generating portion, which are sequentially arranged from a distal-end side along a longitudinal axis, the force transmitting mechanism comprising: a force adjusting portion that is disposed between the joint portion and the force generating portion, that transmits the force applied from the force generating portion, and that is configured to change the force transmission efficiency; and a driving member that passes through the joint portion, that connects the end effector and the force adjusting portion, and that transmits the force applied from the force adjusting portion to the end effector, wherein, by means of a displacement of the driving member in a direction along the longitudinal direction in association with flexing or bending of the joint portion, the force adjusting portion increases the force transmission efficiency so that an amount of increase in the force transmission efficiency increases with the displacement amount of the driving member.

A second aspect of the present invention is directed to an instrument including: an end effector, a joint portion that is configured to flexed or curved, and a force generating portion that generates force, which are sequentially arranged from a distal-end side along a longitudinal axis; and any one of the force transmitting mechanisms described above.

DESCRIPTION OF EMBODIMENT

A force transmitting mechanism 1 and an instrument 2 according to an embodiment of the present invention will be described below with reference to the drawings.

Figure 1:
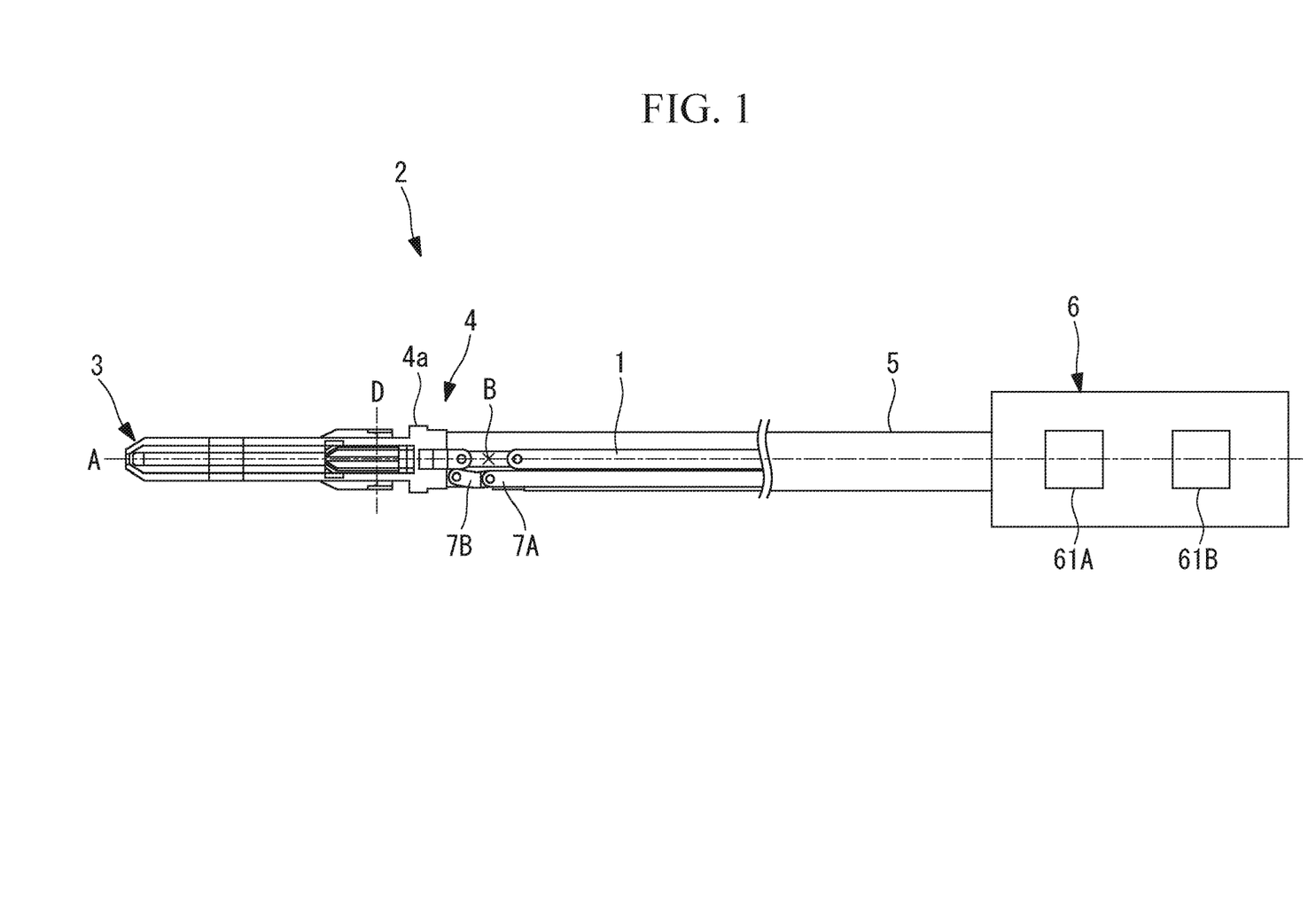
FIG. 1 is an overall configuration diagram of an instrument according to an embodiment of the present invention.

As shown in FIG. 1, the instrument 2 according to this embodiment includes, sequentially arranged along a longitudinal axis A from a distal-end side: an end effector 3; a joint portion 4 that can be flexed about a flexing axis B that is orthogonal to the longitudinal axis A; a long, thin inserted portion 5 that can be inserted into a body along the longitudinal axis A; and an operating portion 6 that generates force for driving the end effector 3 and the joint portion 4 by being operated by an operator.

In addition, the instrument 2 includes the force transmitting mechanism 1, which passes through inside the joint portion 4 and the inserted portion 5, which connects the end effector 3 and the operating portion 6, and which transmits the force to the end effector 3 from the operating portion 6.

The end effector 3 is grasping forceps having a pair of grasping pieces that open/close by being pivoted about a pivoting axis D with respect to each other. The end effector 3 opens due to a pressing force toward the distal end, transmitted from the force transmitting mechanism 1, and closes due to a pulling force toward the proximal end, transmitted from the force transmitting mechanism 1. Therefore, the magnitude of a grasping force generated by the end effector 3 is controlled by the pulling force from the force transmitting mechanism 1.

Note that the end effector 3 is not limited to grasping forceps, other types of end effectors that execute a mechanical motion in accordance with the force (for example, a knife) may be equipped. Alternatively, the joint portion provided in the end effector 3 may be driven by the force from the force transmitting mechanism 1.

At a distal end of the inserted portion 5, the joint portion 4 includes a pivoting member 4a that is supported so as to be pivotable about the flexing axis B. The end effector 3 is attached to the pivoting member 4a, and the end effector 3 is pivoted about the flexing axis B as a result of the pivoting member 4a being pivoted.

Reference signs 7A and 7B indicate a pair of linkages for connecting the pivoting member 4a and the operating portion 6 and transmitting a motive force for pivoting the pivoting member 4a to the pivoting member 4a from the operating portion 6. The first linkage 7A, which is long and is disposed on the proximal-end side, is disposed in a direction along the longitudinal axis A. The second linkage 7B, which is short and is disposed on the distal-end side, is linked to the first linkage 7A and the pivoting member 4a so as to be pivotable about an axis that is parallel to the flexing axis B. As a result of the first linkage 7A being pushed out toward the distal end or being pulled toward the proximal end by the force transmitted to the proximal-end portion of the first linkage 7A from the operating portion 6, the pivoting member 4a pivots about the flexing axis B.

The operating portion 6 includes a first handle 61A for operating the end effector 3 and a second handle 61B for operating the joint portion 4. The operating portion 6 transmits force applied to the first handle 61A as a result of the operator operating the first handle 61A to a second linkage 12B of the force transmitting mechanism 1, described later, in the form of force that acts in a direction along the longitudinal axis A. In addition, the operating portion 6 transmits force applied to the second handle 61B as a result of the operator operating the second handle 61B to the first linkage 7A in the form of force that acts in a direction along the longitudinal axis A. As such handles 61A and 61B, it is possible to employ, for example, handles of arbitrary forms such as lever-type or rotating-type handles.

Figure 2:
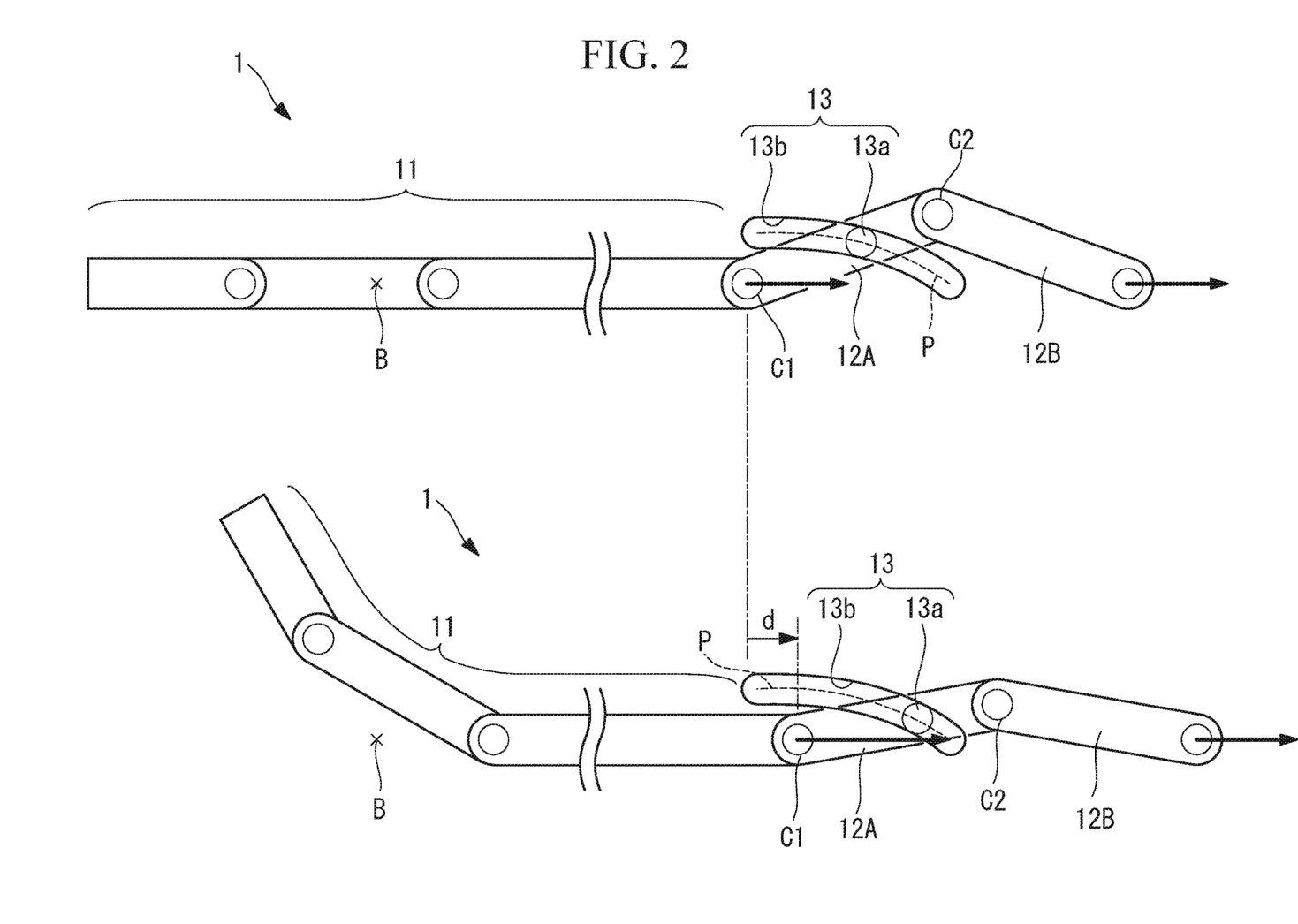
FIG. 2 is a configuration diagram of a force transmitting mechanism of the instrument in FIG. 1, and is a diagram for explaining the motion of the force transmitting mechanism between a state in which joint portions are not flexed (top) and a state in which the joint portions are flexed (bottom).

As shown in FIG. 2, the force transmitting mechanism 1 includes: a driving member 11 that is disposed farther on the proximal-end side than the joint portion 4 is and that is connected to the end effector 3; a first linkage (force adjusting portion) 12A, which is disposed on a proximal-end side of the driving member 11; the second linkage (force adjusting portion) 12B which is disposed on a proximal-end side of the first linkage 12A; and a support portion (force adjusting portion) 13 that supports the first and second linkages 12A and 12B in a movable and pivotable manner. In FIG. 2, the left side is the distal-end side of the instrument 2, and the right side is the proximal-end side of the instrument 2.

The pair of linkages 12A and 12B can be provided at an arbitrary position between the joint portion 4 and the operating portion 6. Therefore, a force transmitting member (for example, a wire or a linkage) for transmitting force to the second linkage 12B from the operating portion 6 may be provided between the second linkage 12B and the operating portion 6, as needed.

The driving member 11 consists of an elongated member that is disposed so as to pass through the joint portion 4 and extend from the end effector 3 to the inserted portion 5, and a distal-end portion of the driving member 11 is connected to the end effector 3. Therefore, the driving member 11 is capable of transmitting the force in the longitudinal direction with high efficiency and of being flexed or curved at the joint portion 4. For example, the driving member 11 is formed of a plurality of linkages that are linked with each other in a pivotable manner or a wire that possesses flexibility. As a result of the driving member 11 being moved forward toward the distal end, the pressing force (force) for causing the end effector 3 to open is applied to the end effector 3, and, as a result of the driving member 11 being retracted toward the proximal end, the pulling force (force) for causing the end effector 3 to close is applied to the end effector 3.

The first linkage 12A and the second linkage 12B are members that are elongated in the longitudinal direction. A proximal-end portion of the driving member 11 and a distal-end portion of the first linkage 12A are linked so as to be pivotable about a first pivoting axis C1 that is orthogonal to the longitudinal axis A. A proximal-end portion of the first linkage 12A and a distal-end portion of the second linkage 12B on the proximal-end side are linked so as to be pivotable about a second pivoting axis C2 that is parallel to the first pivoting axis C1. Although the attached drawings show examples in which the flexing axis B and the pivoting axes C1 and C2 are parallel to each other, the flexing axis B and the pivoting axes C1 and C2 need not be parallel to each other. The proximal-end portion of the second linkage 12B is supported by a peripheral member (not shown) so as to move only in the direction along the longitudinal axis A (for example, so as to move along an extension of the longitudinal axis of the driving member 11) in accordance with the force transmitted from the operating portion 6.

The support portion 13 includes: a pin (protruding member) 13a that is secured to the first linkage 12A between the pivoting axis C1 and the pivoting axis C2 and that protrudes substantially parallel to the pivoting axes C1 and C2; and a long, thin slit (guiding pathway) 13b that extends from the distal-end side to the proximal-end side and that guides the pin 13a so the that the pin 13a moves along a predetermined moving path P. The slit 13b is formed in, for example, a member (not shown) that is secured inside the inserted portion 5 and that is in an area surrounding the first linkage 12A. In the slit 13b, the pin 13a can move on the predetermined moving path P defined by the shape of the slit 13b. In this way, the pin 13a inserted into the slit 13b in a movable manner supports the first linkage 12A and the second linkage 12B so as to be movable in directions along the longitudinal axis A.

Next, motions of the driving member 11, the first linkage 12A, and the second linkage 12B and the shape of the slit 13b will be described for the case in which the joint portion 4 is flexed about the flexing axis B.

In FIG. 2, a state in which the joint portion 4 is not flexed (a state in which the end effector 3 and the inserted portion 5 are disposed so as to be lined up in a straight line) is shown at the top, and a state in which the joint portion 4 is flexed is shown at the bottom. The position of the driving member 11 in the state in which the joint portion 4 is not flexed will be defined as the reference position.

Figure 3:
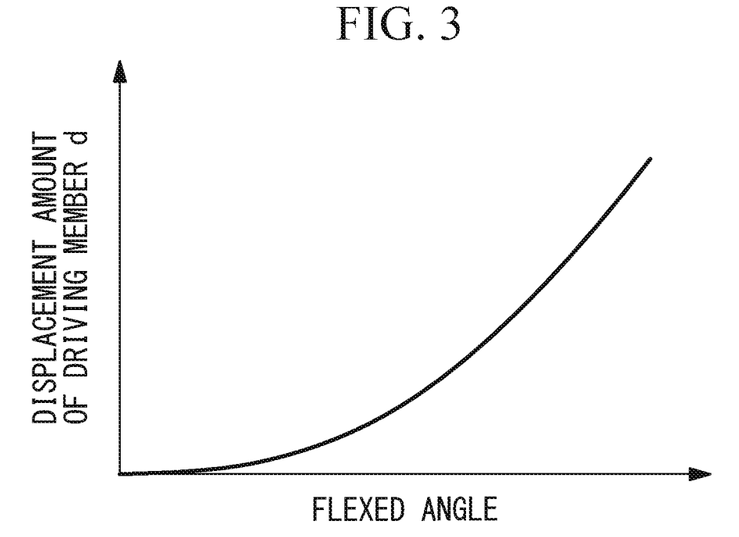
FIG. 3 is a graph showing the relationship between the flexed angle of a joint portion and the displacement amount of the driving member.

When the joint portion 4 is flexed about the flexing axis B, as shown in FIG. 2, the length of the path in which the driving member 11 is disposed changes, the driving member 11 is displaced toward the proximal end from the reference position, and the first linkage 12A and the second linkage 12B also move toward the proximal end. A displacement amount d of the driving member 11 increases with an increase in the flexed angle of the joint portion 4, as shown in FIG. 3.

Here, the position and the shape of the slit 13b are designed so that, in the state in which the joint portion 4 is not flexed, the first linkage 12A and the second linkage 12B are disposed in an inclined manner with respect to the longitudinal axis A so as to form an angle γ with respect to each other (see FIG. 4), and so that the angle γ decreases in association with movement toward the proximal end (so that the longitudinal directions of the first and second linkages 12A and 12B respectively approach directions that are parallel to the longitudinal axis A). The angle γ is an angle formed between the longitudinal direction of the first linkage 12A and the longitudinal direction of the second linkage 12B.

Figure 4:
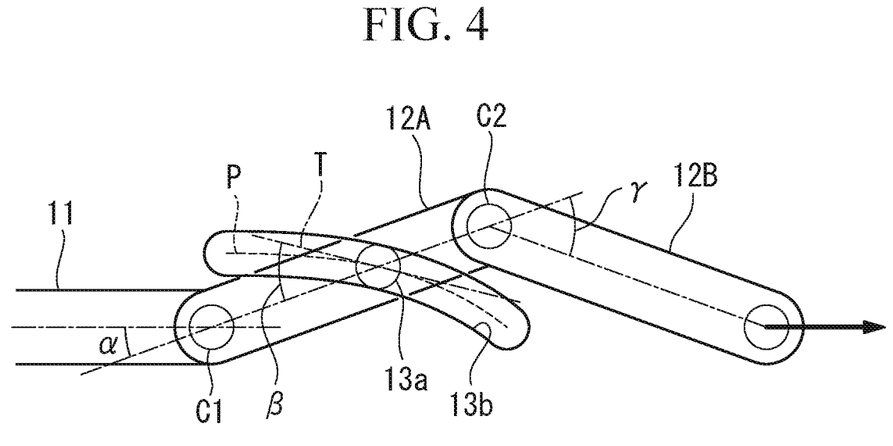
FIG. 4 is a diagram for explaining the relationship between angles of a first linkage and a second linkage of the force transmitting mechanism and the shape of a slit.

In addition, as shown in FIG. 4, the shape of the slit 13*b* is designed so that an angle α continuously, monotonically decreases and an angle β increases with an increase in the displacement amount d of the driving member 11 toward the proximal end. The angle α is an angle formed between the longitudinal direction of the first linkage 12A and the longitudinal direction (longitudinal axis A) of the driving member 11. The angle β is an angle formed between the longitudinal direction of the first linkage 12A and a tangent T on the moving path P of the slit 13*b* (at an intersection of the longitudinal axis of the first linkage 12A and the moving path P). Therefore, the slit 13*b* has a curved shape in which the inclination of the tangent T gradually changes from a distal end of the slit 13*b* toward the proximal end thereof so that, on the distal-end side, the direction of the tangent T approaches a direction that is parallel to the longitudinal axis A, and so that, on the proximal-end side, the direction of the tangent T approaches a direction that is orthogonal to the longitudinal axis A. Accordingly, with an increase in the flexed angle of the joint portion 4, the angle α approaches 0°, and the angle β approaches 90°.

Furthermore, the shape (moving path P) of the slit 13*b* is designed so as that the angles α, β, and γ respectively satisfy the following expressions (1), (2), and (3).

$$0° \leq \alpha < 90° \quad (1)$$

$$0° \leq \beta < 90° \quad (2)$$

$$0° \leq \gamma < 90° \quad (3)$$

As a result of the angles α, β, γ satisfying the above-described ranges, it is possible to avoid a singular point at which the linkages 12A and 12B do not move appropriately, and to smoothly move the linkages 12A and 12B in the moving range of the pin 13*a*.

Figure 5:
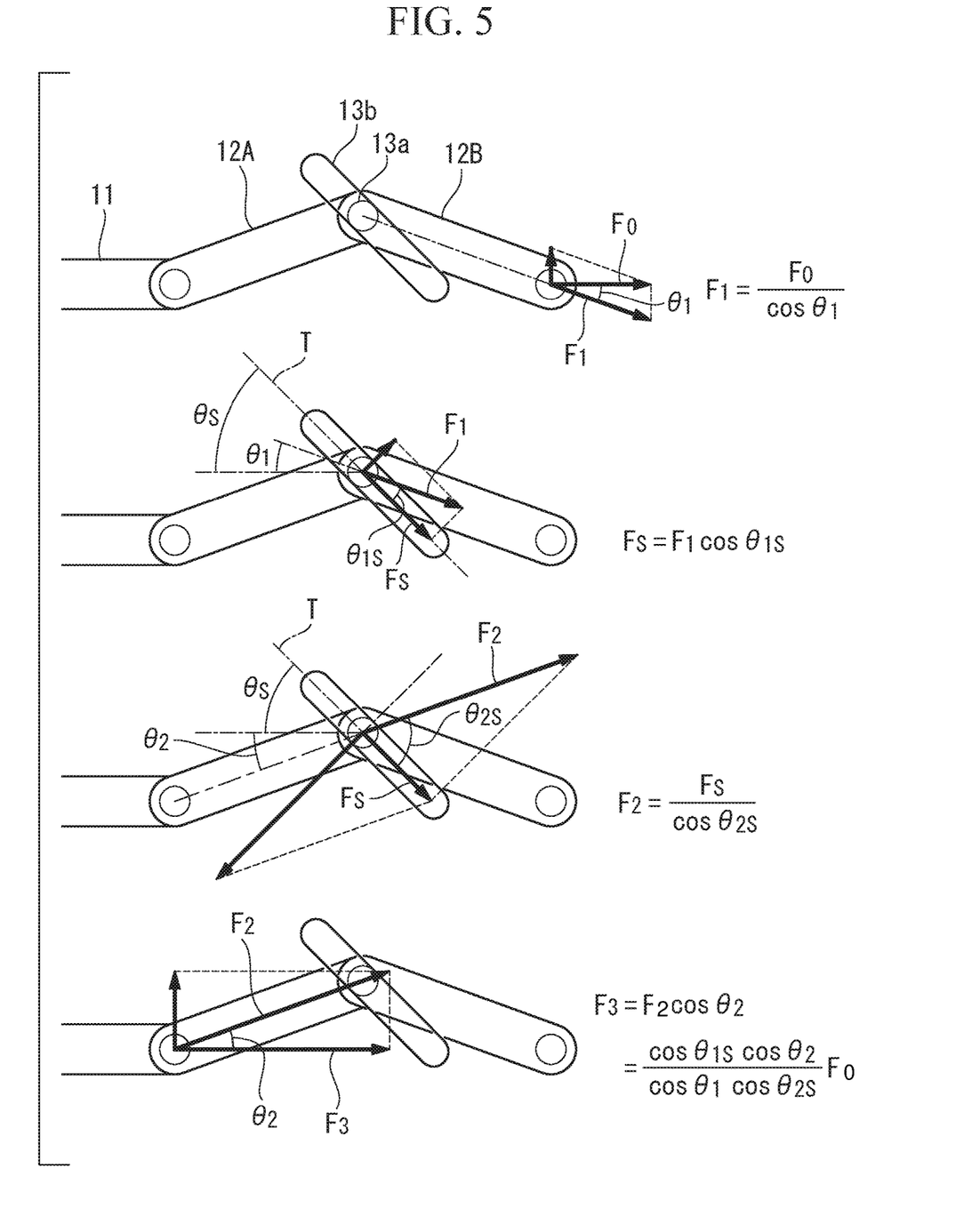
FIG. 5 is a diagram for explaining the transmission of force in the first linkage and the second linkage.

FIG. 5 shows the relationship between a force F0 that is applied to the second linkage 12B from the operating portion 6 and that acts in the direction of the longitudinal axis A and a force F3 that is applied to the driving member 11 from the first linkage 12A and that acts in the direction of the longitudinal axis A. In order to simplify the description, FIG. 5 shows a slit 13*b* that has a linear shape in which an angle θs of the tangent T is constant. In FIG. 5, α=θ2, β=θs+θ2, and γ=θ1+θ2. As is clear from FIG. 5, the force F0 applied to the second linkage 12B increases with efficiencies in accordance with the angles θ1 and θ2 of the linkages 12A and 12B and the angle θs of the tangent T of the slit 13*b* in the process of being transmitted through the second linkage 12B and the first linkage 12A. Specifically, by controlling the angles θ1, θ2, and θs by means of the shape of the slit 13*b*, it is possible to control the force transmission efficiencies of the first linkage 12A and the second linkage 12B.

Figure 6:
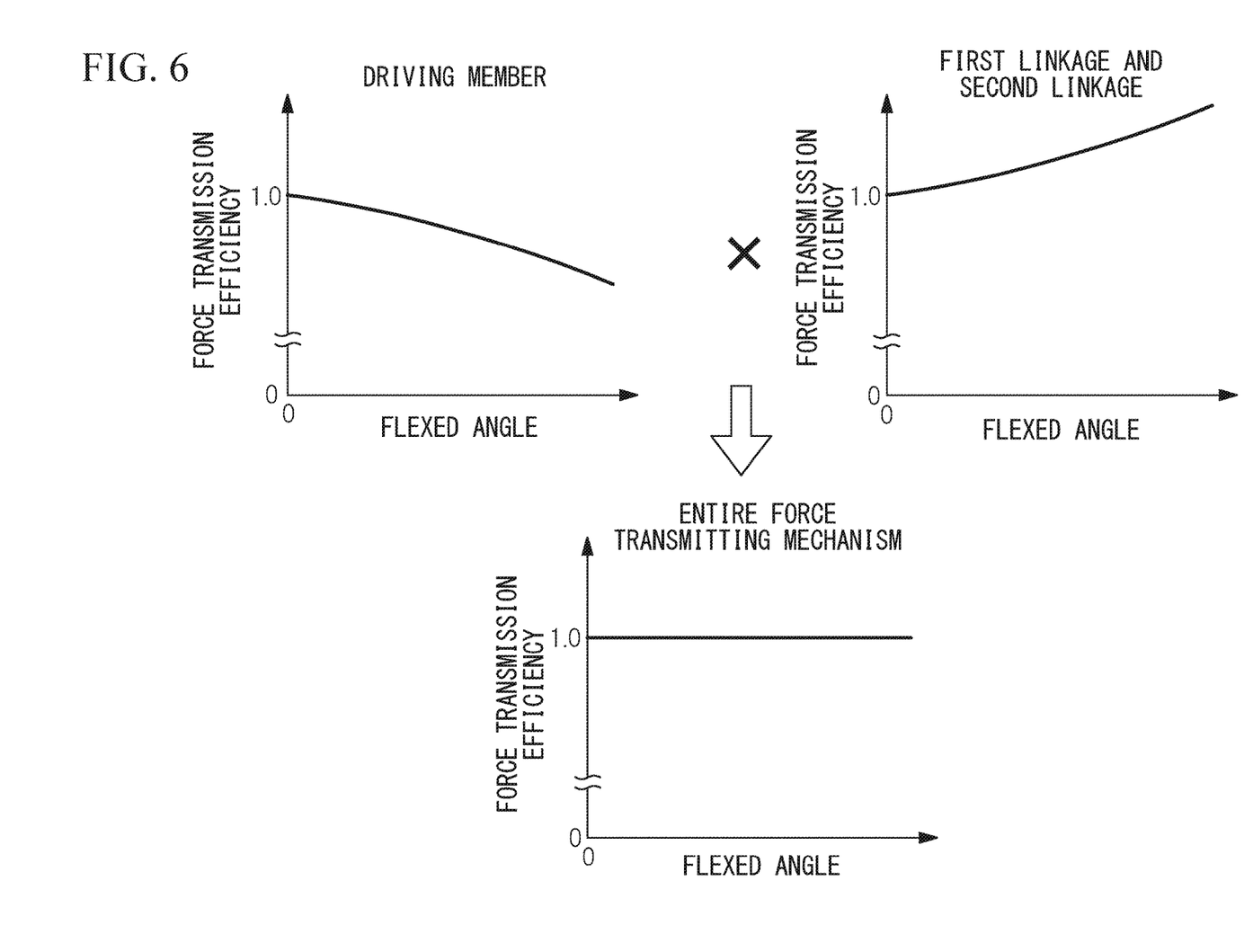
FIG. 6 shows graphs indicating the relationships between the flexed angles of the joint portion and the force transmission efficiency of the driving member, the first and second linkages, and the entire force transmitting mechanism.

FIG. 6 shows changes in the force transmission efficiencies of the driving member 11, the linkages 12A and 12B, and the entire force transmitting mechanism 1 with respect to changes in the flexed angle of the joint portion 4. As shown in FIG. 6, the force transmission efficiency of the driving member 11 decreases with an increase in the flexed angle of the joint portion 4. This is because a loss occurs in the force transmitted through the driving member 11 as a result of an increase in the friction between the flexed driving member 11 and the peripheral member. The above-described decrease in the force transmission efficiency occurs also in a component of the force that acts in the direction orthogonal to the longitudinal axis A in accordance with the angle between the linkages because a loss occurs, as a result of flexing of linkages constituting the driving member 11.

The force transmission efficiencies of the first linkage 12A and the second linkage 12B increase with an increase in the flexed angle of the joint portion 4 as a result of appropriately designing the curved shape of the slit 13*b*.

Specifically, the force transmission efficiency of the entire force transmitting mechanism 1 is expressed as the product of the force transmission efficiencies of the first linkage 12A and the second linkage 12B and the force transmission efficiency of the driving member 11. The amounts by which the force transmission efficiencies of the first second linkages 12A and 12B increase are designed in consideration of the amount of decrease in the force transmission efficiency of the driving member 11 so that, at any flexed angle of the joint portion 4, the force transmission efficiencies of the first and second linkages 12A and 12B becomes substantially equal to the inverse of the force transmission efficiency of the driving member 11. By doing so, the force transmission efficiency of the entire force transmitting mechanism 1 is maintained to be constant regardless of the flexed angle of the joint portion 4.

Figure 7:
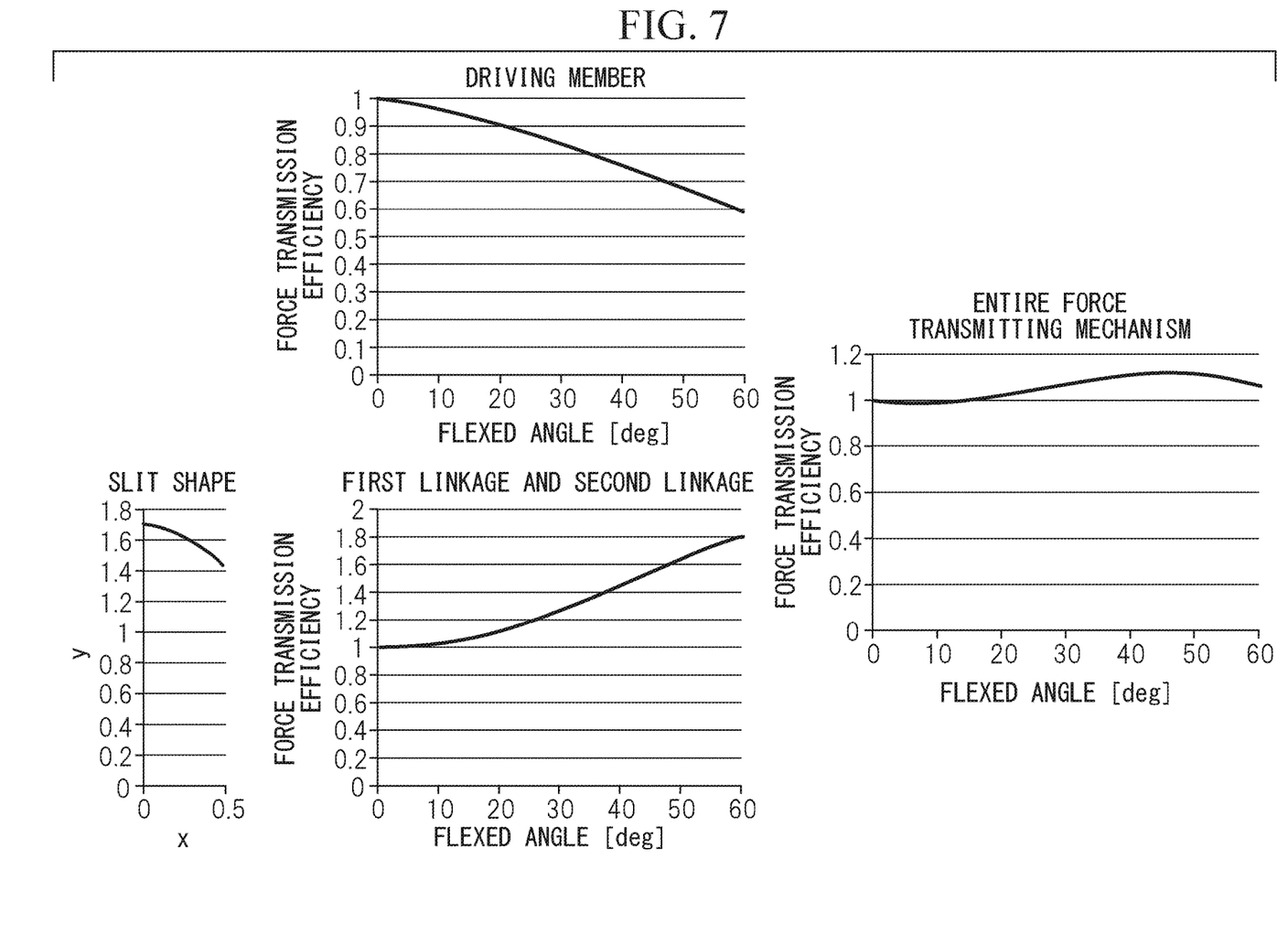
FIG. 7 is a diagram showing the force transmission efficiency of the driving member, the first and second linkages, and the entire force transmitting mechanism and an example of the slit shape.

FIG. 7 shows, as examples of design values of the slit 13*b* in this embodiment, example force transmission efficiencies of the driving member 11, the linkages 12A and 12B, and the entire force transmitting mechanism 1.

Next, the operations of the force transmitting mechanism 1 and the instrument 2, thus configured, will be described.

In order to treat an affected portion by using the instrument 2 of this embodiment, the inserted portion 5 is inserted into a body, the end effector 3 at the distal end is disposed in the vicinity of the affected portion, and the attitude of the end effector 3 with respect to the affected portion is adjusted by flexing the joint portion 4 by operating the second handle 61B of the operating portion 6.

Next, the first handle 61A provided in the operating portion 6 is operated, and the affected portion is grasped by using the end effector 3. At this time, force corresponding to the amount of operation applied to the first handle 61A is transmitted to the end effector 3 from the operating portion 6 via the second linkage 12B, the first linkage 12A, and the driving member 11, and thus, the end effector 3 grasps the affected portion with a grasping force, the magnitude of which corresponds to the force applied to the end effector 3.

In this case, in the state in which the joint portion 4 is flexed, the degree of contact between the driving member 11, which is flexed (or curved) together with the joint portion 4, and the peripheral member increases, which increases the friction between the driving member 11 and the peripheral member, and thus, the force transmission efficiency of the driving member 11 decreases. In the case in which the driving member 11 is formed of a plurality of linkages, additional losses of the force transmission efficiency occur in accordance with angles among the linkages. With an increase in the flexed angle of the joint portion 4, the amount of decrease in the force transmission efficiency of the driving member 11 also increases. On the other hand, in the state in which the joint portion 4 is flexed, the angles α, β, and γ of the linkages 12A and 12B, which are disposed on the transmission path of the force, change due to the displacement of the driving member 11 from the reference position, and thus, the force transmission efficiencies of the linkages 12A and 12B increase. With an increase in the flexed angle of the joint portion 4, the amount of increase in the force transmission efficiency of the connecting member 12 also increases.

As has been described above, as a result of the decrease in the force transmission efficiency of the driving member 11 associated with flexing of the joint portion 4 being compensated by the increase in the force transmission efficiencies of the linkages 12A and 12B, the force transmission efficiency of the entire force transmitting mechanism 1 becomes constant regardless of the flexed angle of the joint portion 4. Specifically, regardless of the flexed angle of the joint portion 4, the relationship between the amount of operation applied to the first handle 61A and the grasping force of the end effector 3 is maintained constant. Therefore, there is an advantage in that the operator can accurately control the grasping force by means of the amount of operation applied to the first handle 61A.

Figure 8:
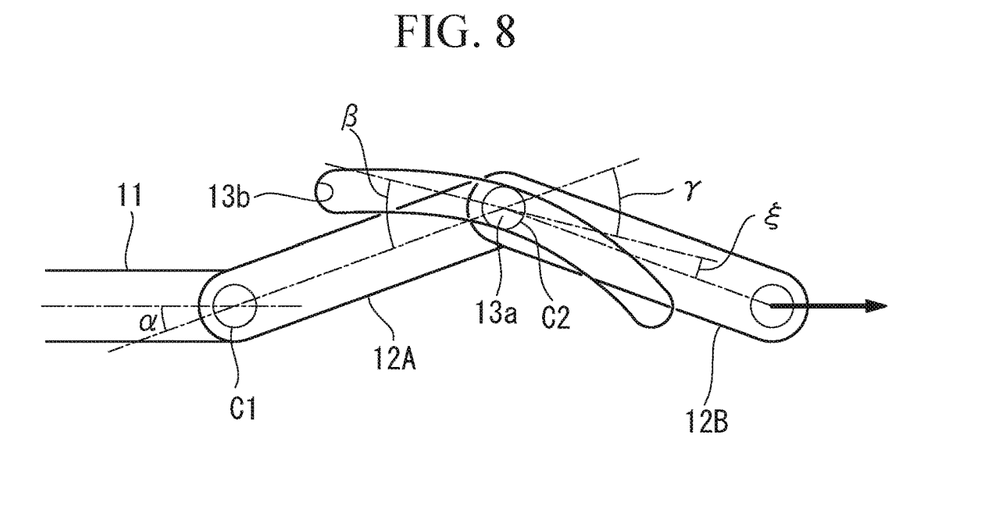
FIG. 8 is a configuration diagram of a modification of the force transmitting mechanism.

In this embodiment, although the pin 13a is provided in the first linkage 12A between the first pivoting axis C1 and the second pivoting axis C2, alternatively, the pin 13a may be provided on the second pivoting axis C2, as shown in FIG. 8.

As has been described above, because protruding amounts of the proximal-end portion of the first linkage 12A and the distal-end portion of the second linkage 12B decrease as a result of providing the pin 13a on the pivoting axis C2 positioned radially outside with respect to the driving member 11, it is possible to make the entire force transmitting mechanism 1 be a structure having a smaller diameter.

In the configuration in which the pin 13a is provided on the pivoting axis C2, it is preferable that expression (4) below be satisfied in addition to the above-described expressions (1), (2), and (3). An angle ξ is an angle formed between the longitudinal axis of the second linkage 12B and the tangent T of the moving path P.

$$-90° \leq \xi < 90° \quad (4)$$

By doing so, it is possible to avoid a singular point at which the linkages 12A and 12B do not move appropriately, and to smoothly move the linkages 12A and 12B in the moving range of the pin 13a.

In addition, the pin 13a may be provided in the second linkage 12B instead of the first linkage 12A. In this case also, it is possible to increase the force transmission efficiencies of the linkages 12A and 12B due to the displacement of the driving member 11 as a result of appropriately designing the curved shape of the slit 13b.

In this embodiment, although the linkage mechanism including the pair of linkages 12A and 12B is employed as the force adjusting portion that adjusts the force transmission efficiency form the operating portion 6 to the driving member 11, it is possible to employ an arbitrary configuration so long as it is possible to increase the force transmission efficiency in accordance with the displacement amount d of the driving member 11 toward the proximal end.

Figure 9:
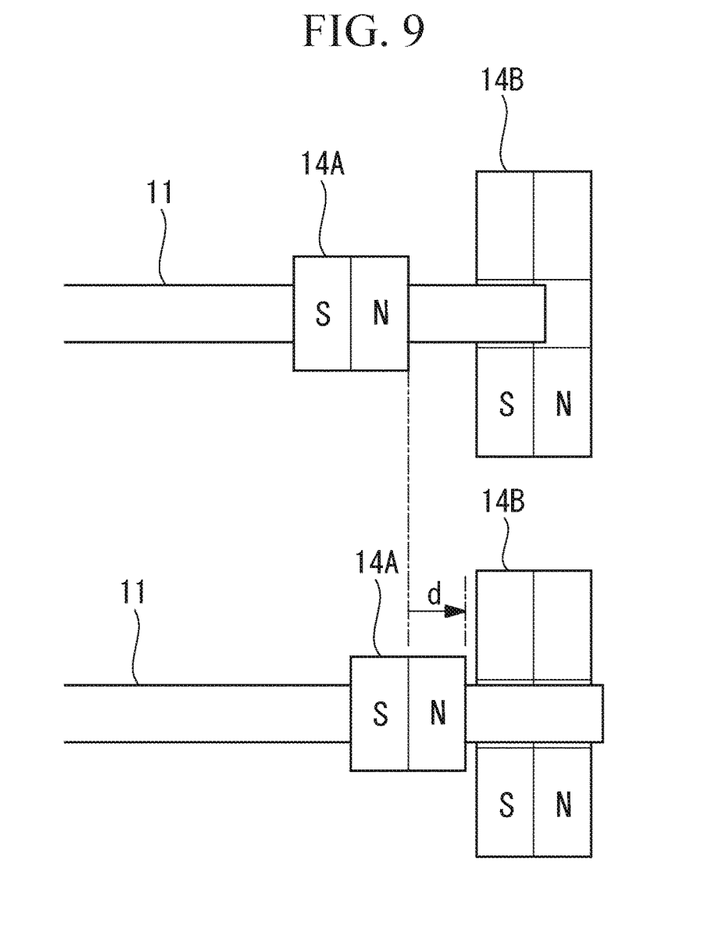
FIG. 9 is a configuration diagram of another modification of the force transmitting mechanism.

For example, as shown in FIG. 9, the force adjusting portion may include a pair of magnets 14A and 14B that generate attractive forces with respect to each other. The magnet 14A is provided in the driving member 11, and the other magnet 14B is disposed farther on the proximal-end side than the magnet 14A is and is connected to the operating portion 6. Accordingly, when the driving member 11 is displaced toward the proximal end, the magnetic force between the magnets 14A and 14B increases, and, as a result, it is possible to increase the force transmission efficiency.

In this embodiment, although the joint portion 4 having a single flexing axis B is provided, the specific form of the joint portion 4 is not limited thereto, and other forms of joint portions that can be flexed or curved in a direction that intersects the longitudinal axis of the inserted portion 5 may be employed.

For example, the joint portion may be a bending portion: that has a plurality of flexing axes that are arrayed in the direction along the longitudinal axis A and that are parallel to each other, and that can be curved at a relatively large radius of curvature, or the joint portion may be a bending portion that can be curved by virtue of possessing flexibility.

In addition, the joint portion may constitute the inserted portion 5 possessing flexibility, and the force transmitting mechanism 1 may increase the force transmission efficiency in accordance with a curved angle of the inserted portion 5 in the body. When the inserted portion 5 changes from the linear shape to a curved shape, the path length of the driving member 11, such as a wire that passes through inside the inserted portion 5, changes, and the driving member 11 is displaced in the longitudinal direction. Therefore, for example, as a result of providing the force transmitting mechanism 1 in the proximal-end portion, which is a portion of the inserted portion 5 that is disposed outside the body, it is possible to compensate for the decrease in the force transmission efficiency of the driving member 11 associated with the bending of the inserted portion 5 by means of the increase in the force transmission efficiency of the force transmitting mechanism 1 in accordance with the displacement of the driving member 11.

In this embodiment, although the operating portion 6 that generates force by means of manual operation by the operator is provided, alternatively, a driving portion that generates force by means of an electric motor may be employed as the force generating portion. For example, an operation input device (not shown) that is separate from the instrument 2 may be provided; when the operator inputs an operating signal for moving the end effector 3 to the operation input device, the input operating signal may be transmitted to the driving portion from the operation input device; and the electric motor may generate force corresponding to the operating signal.

As a result, the above-described embodiment leads to the following aspects.

A first aspect of the present invention is a force transmitting mechanism that is provided in an instrument including an end effector, a joint portion that is configured to be flexed or curved, and a force generating portion that generates force and that transmits the force to the end effector from the force generating portion, which are sequentially arranged from a distal-end side along a longitudinal axis, the force transmitting mechanism comprising: a force adjusting portion that is disposed between the joint portion and the force generating portion, that transmits the force applied from the force generating portion, and that is configured to change the force transmission efficiency; and a driving member that passes through the joint portion, that connects the end effector and the force adjusting portion, and that transmits the force applied from the force adjusting portion to the end effector, wherein, by means of a displacement of the driving member in a direction along the longitudinal direction in association with flexing or bending of the joint portion, the force adjusting portion increases the force transmission efficiency so that an amount of increase in the force transmission efficiency increases with the displacement amount of the driving member.

With the first aspect of the present invention, as a result of the force generated by the force generating portion being transmitted to the end effector via the force adjusting portion and the driving member, it is possible to cause the end effector to execute a mechanical motion.

In this case, as a result of the driving member, which is disposed across the joint portion, also being flexed or curved when the joint portion is flexed or curved, the driving member is displaced in the direction along the longitudinal direction of the instrument, and the force transmission efficiency decreases. Also, in response to the displacement of the driving member, the force transmission efficiency of the force adjusting portion increases so that the force transmission efficiency of the force adjusting portion increases with an increase in the displacement amount of the driving member.

With an increase in flexing of the joint portion or a bending angle of the joint portion, both the displacement amount of the driving member and the amount of decrease in the force transmission efficiency increase. Therefore, by increasing the amount of increase in the force transmission efficiency of the force adjusting portion in accordance with the displacement amount of the driving member, it is possible to favorably compensate for the decrease in the force transmission efficiency of the driving member with the increase in the force transmission efficiency of the force adjusting portion. By doing so, it is possible to transmit the force to the end effector at a constant efficiency regardless of flexing or bending of the joint portion.

In the above-described first aspect, the force adjusting portion may increase the force transmission efficiency so that the force transmission efficiency of the force adjusting portion becomes substantially equal to the inverse of the force transmission efficiency of the driving member.

The force transmission efficiency of the entire force transmitting mechanism is expressed as the product of the force transmission efficiency of the force adjusting portion and the force transmission efficiency of the driving member. Therefore, as a result of the force transmission efficiency of the force adjusting portion increasing so as to be substantially equal to the inverse of the decreased force transmission efficiency of the driving member due to flexing or bending of the joint portion, it is possible to accurately make the force transmission efficiency of the entire force transmitting mechanism constant regardless of flexing or bending of the joint portion.

In the above-described first aspect, the force adjusting portion may include: a first linkage that is disposed on a proximal-end side of the driving member, and that is linked to the driving member so as to pivot about a first pivoting axis that intersects the longitudinal axis; a second linkage that is disposed on a proximal-end side of the first linkage, and that is linked to the first linkage so as to pivot about a second pivoting axis that is parallel to the first pivoting axis; and a support portion that supports the first linkage and the second linkage so as to pivot with respect to each other and so as to move in directions along the longitudinal axis, wherein the support portion supports the first linkage and the second linkage so that an angle between the first linkage and the second linkage changes in accordance with the displacement of the driving member.

By doing so, when the driving member is displaced due to flexing or bending of the joint portion, the first linkage and the second linkage pivot with respect to each other and move while changing the angle between the first and second linkages. In the first and second linkages, the force applied to the first linkage from the force generating portion increases in accordance with the angle between the first linkage and the second linkage. In this way, it is possible to increase the force transmission efficiency by utilizing only mechanical mechanisms.

In the above-described first aspect, the support portion may include: a protruding member that is provided in the first linkage or the second linkage and that protrudes substantially parallel to the first pivoting axis; and a guiding pathway into which the protruding member is inserted, and that guides movement of the protruding member so that the protruding member moves on a predetermined moving path.

By doing so, it is possible to control, with a simple configuration, movement and pivoting of the first linkage and second linkage associated with displacement of the driving member.

In the above-described first aspect, an angle $\alpha$ formed between the first linkage and the driving member, an angle $\beta$ formed between the first linkage and a tangent of the predetermined moving path, and an angle $\gamma$ formed between the first linkage and the second linkage satisfy the following relational expressions:

$$0° \leq \alpha < 90°;$$

$$0° \leq \beta < 90°; \text{ and}$$

$$0° \leq \gamma < 90°.$$

By doing so, it is possible to avoid disposing the first linkage and the second linkage at a singular point at which the first linkage and the second linkage do not move in accordance with the force, and it is possible to cause the first linkage and the second linkage to smoothly execute motions.

In the above-described first aspect, the protruding member may be provided on the second pivoting axis.

By doing so, it is possible to reduce the size of the force adjusting portion by minimizing protruding amounts of the first linkage and the second linkage in directions that intersect the longitudinal axis.

In the above-described first aspect, an angle $\xi$ formed between the second linkage and the tangent of the predetermined moving path satisfies the following relational expression:

$$-90° \leq \xi < 90°.$$

By doing so, it is possible to avoid disposing the first linkage and the second linkage at a singular point at which the first linkage and the second linkage do not move in accordance with the force, and the first linkage and the second linkage smoothly execute motions.

A second aspect of the present invention is an instrument including: an end effector, a joint portion that is configured to be flexed or curved, and a force generating portion that generates force, which are sequentially arranged from a distal-end side along a longitudinal axis; and any one of the force transmitting mechanisms described above.

The present invention affords an advantage in that it is possible to transmit force to an end effector at a constant efficiency regardless of flexing or bending of a joint portion.

REFERENCE SIGNS LIST 1 force transmitting mechanism
2 instrument
3 end effector 4 joint portion
5 inserted portion
6 operating portion
7A,7B linkage
11 driving member
12A first linkage (force adjusting portion)
12B second linkage (force adjusting portion)
13 support portion (force adjusting portion)
13a pin (protruding member, support portion, force adjusting portion)
13b slit (guiding pathway, support portion, force adjusting portion)
14A,14B magnet (force adjusting portion)
C1 first pivoting axis
C2 second pivoting axis
P moving path
T tangent

The invention claimed is:

1. A force transmitting mechanism provided in an instrument including an end effector, a joint configured to be flexed or curved, and a force generating portion that generates force and that transmits the force to the end effector from the force generating portion, the end effector, joint and force generating portion being sequentially arranged from a distal-end side to a proximal end side along a longitudinal axis, the force transmitting mechanism comprising:
   a force adjusting portion disposed between the joint and the force generating portion, the force adjusting portion being configured to transmit the force applied from the force generating portion and to change a force transmission efficiency; and
   an elongated driving member that passes through the joint, the driving member being configured to connect the end effector and the force adjusting portion and that to transmit the force applied from the force adjusting portion to the end effector,
   wherein, by means of a displacement of the driving member in a direction along the longitudinal direction in association with flexing or bending of the joint, the force adjusting portion increases the force transmission efficiency so that an amount of increase in the force transmission efficiency increases with the displacement amount of the driving member;
   the force adjusting portion comprises:
      a first linkage disposed on a proximal-end side of the driving member, the first linkage being linked to the driving member so as to pivot about a first pivoting axis that intersects the longitudinal axis;
      a second linkage disposed on a proximal-end side of the first linkage, the second linkage being linked to the first linkage so as to pivot about a second pivoting axis that is parallel to the first pivoting axis; and
      a support configured to support the first linkage and the second linkage so as to pivot with respect to each other and so as to move in directions along the longitudinal axis, and
   the support supports the first linkage and the second linkage so that an angle between the first linkage and the second linkage changes in accordance with the displacement of the driving member.

2. The force transmitting mechanism according to claim 1, wherein the force adjusting portion is configured to increase the force transmission efficiency so that the force transmission efficiency of the force adjusting portion becomes substantially equal to an inverse of the force transmission efficiency of the driving member.

3. The force transmitting mechanism according to claim 1,
   wherein the support includes:
      a protrusion provided in one of the first linkage or the second linkage, the protrusion protruding substantially parallel to the first pivoting axis; and
      a guiding pathway into which the protrusion is inserted, the guiding pathway being configured to guide movement of the protrusion so that the protrusion moves on a predetermined moving path.

4. The force transmitting mechanism according to claim 3, wherein an angle $\alpha$ formed between the first linkage and the driving member, an angle $\beta$ formed between the first linkage and a tangent of the predetermined moving path, and an angle $\gamma$ formed between the first linkage and the second linkage satisfy the following relational expressions:

$$0°\leq\alpha<90°$$

$$0°\leq\beta<90°$$

$$0°\leq\gamma<90°$$

5. The force transmitting mechanism according to claim 4, wherein the protrusion is provided on the second pivoting axis.

6. The force transmitting mechanism according to claim 5, wherein an angle $\xi$ formed between the second linkage and the tangent of the predetermined moving path satisfies the following relational expression:

$$-90°\leq\xi<90°$$

7. An instrument comprising:
   the force transmitting mechanism according to claim 1 that transmits the force to the end effector from the force generating portion; and
   the end effector, the joint that is configured to be flexed or curved, and the force generating portion that generates force.

* * * * *